United States Patent [19]

Cermak et al.

[11] 4,151,503

[45] Apr. 24, 1979

[54] TEMPERATURE COMPENSATED RESISTIVE EXHAUST GAS SENSOR CONSTRUCTION

[75] Inventors: Michael J. Cermak, Southfield; Stanley R. Merchant, Garden City, both of Mich.

[73] Assignee: Ford Motor Company, Dearborn, Mich.

[21] Appl. No.: 839,704

[22] Filed: Oct. 5, 1977

[51] Int. Cl.² ........................................... G01N 27/12
[52] U.S. Cl. ........................................ 338/14; 73/23; 73/27 R; 204/195 S; 338/22 SD; 338/38
[58] Field of Search .................. 73/27 R, 23; 338/14, 338/22 SD, 38; 204/195 S

[56] References Cited

U.S. PATENT DOCUMENTS

| | | | |
|---|---|---|---|
| 2,928,276 | 3/1960 | Beard | 73/23 |
| 3,186,835 | 6/1965 | Bundy | 338/22 SD |
| 3,459,503 | 8/1969 | Roy | 264/332 X |
| 3,522,010 | 7/1970 | Archer | 73/23 X |
| 3,699,803 | 10/1972 | Sumi | 73/27 R |
| 3,915,135 | 10/1975 | Kushida | 204/195 S |
| 4,007,435 | 2/1977 | Tien | 338/34 |
| 4,029,472 | 6/1977 | Micheli | 23/254 E |

*Primary Examiner*—Richard R. Kucia
*Attorney, Agent, or Firm*—Robert W. Brown; Clifford L. Sadler

[57] ABSTRACT

A pair of ceramic chips, formed of similar metal oxide ceramic materials which are semiconductors at elevated temperature, are connected electrically in series and are arranged for exposure to the hot gaseous combustion by-products produced by an internal combustion engine. The chips are positioned in the exhaust gas conduit by a ceramic insulator having a plurality of longitudinal passages extending therethrough. A plurality of electrical terminal members are received within the rear of the longitudinal passages. Electrical leads extend from the chips to the terminal members through the plurality of passages and support the chips while providing electrical communication between the chips and the electrical terminals. The electrical terminals are adapted for communication to electronic and/or electrical utilization means. One of the pair of chips is processed to exhibit a rapid change in an electrical property responsive to differences in the exhaust gas chemistry and differences in exhaust gas temperature. The other of the chips is processed to exhibit a rapid change in an electrical property responsive to differences in exhaust gas temperature only. The preferred material is titania. For temperatures in the range of from about 700° F. to about 1500° F., the application of a reference voltage across the series connected chips will produce a substantially temperature independent voltage variation across either chip in response to changes in exhaust gas chemistry and which is relatively insensitive to changes in the exhaust gas temperature.

9 Claims, 11 Drawing Figures

TEMPERATURE COMPENSATED RESISTIVE EXHAUST GAS SENSOR CONSTRUCTION

CROSS REFERENCE TO RELATED APPLICATIONS

This application is related to copending commonly filed patent application Ser. No. 839,700 filed in the names of S. R. Merchant and M. J. Cermak and titled Titania Thermistor and Method of Fabricating. This application is also related to copending commonly filed patent application Ser. No. 839,701 filed in the names of W. L. Green, S. R. Merchant and M. J. Esper and titled Catalytic Material Impregnated, Porous Variably Resistive Exhaust Gas Sensor and Method of Impregnation. This application is also related to copending commonly filed patent application Ser. No. 839,706 filed in the name of W. R. McDonald and titled Thermistor Temperature Compensated Titania Exhaust Gas Sensor. These related applications are assigned to the assignee of this application.

BACKGROUND OF THE INVENTION

1. Field of the Invention

The present invention is directed to the field of electrochemical gas analyzers. More particularly, the present invention is directed to that portion of the above-noted field which is concerned with the generation of an electrical signal indicative of a gas chemistry. More specifically still, the present invention is directed to that portion of the above-noted field which is concerned with electrochemical gas sensors responsive to the partial pressure of oxygen in gaseous samples. More particularly still, the present invention is directed to that portion of the above-noted field which is concerned with the generation of an electrical signal indicative of the partial pressure of oxygen within the heated gaseous combustion by-products generated by an internal combustion engine. More particularly still, the present invention is directed to that portion of the above-noted field which is concerned with the generation of an electrical signal which may be rendered relatively insensitive to changes in the temperature of the gaseous comboustion by-products while responding rapidly to variations in the partial pressure of oxygen in the gaseous combustion by-products.

2. Description of the Prior Art

It has been determined that the operation of a conventional automotive internal combustion engine produces substantial quantities of deleterious gaseous combustion by-products. The principal pollutants so produced are hydrocarbons, carbon monoxide and various oxides of nitrogen. Extensive investigation into the combustion process, examination of alternative combustion processes and detailed studies of exhaust gas treatment devices have lead to the conclusion that the use of a catalytic converter within the exhaust system of an internal combustion engine provides a practical and effective technique for substantially reducing the emission of the deleterious gaseous combustion by-products into the atmosphere. A catalytic exhaust treatment device or converter which is capable of substantially simultaneously converting all three of the aforementioned principal pollutants into water, carbon dioxide and gaseous nitrogen is referred to as a "three-way catalyst". However, for the known three-way catalyst devices to be most effective, the gaseous by-products introduced into the converter must be the by-products of combustion of a substantially stoichiometric air/fuel mixture. Such three-way catalysts are said to have a very narrow "window" of air/fuel ratios at which the device is most efficiently operative on the three principal pollutants. By way of example if $\lambda$ is the air/fuel ratio normalized to stoichiometry, the window may extend from about $0.99\lambda$ to about $1.01\lambda$. Such a three-way catalytic converter is described, for example, in U.S. Pat. No. 3,895,093 issued to Weidenbach et at. on July 15, 1975, assigned to KaliChemie Aktiengesellschaft and titled "Catalytic Removal of Carbon Monoxide Unburned Hydrocarbons and Nitrogen Oxides From Automotive Exhaust Gas". For air/fuel ratios of the combustion mixture on either side of the window, one or two of the principal pollutants will be converted in only very small percent efficiencies. Within the window, the three principal pollutants will be converted at very high percent efficiencies approaching 90% in some cases. In view of the narrowness of the catalytic converter window, if has been determined that the associated internal combustion engine must be operated with a combustible mixture as close as possible to stoichiometry.

The most satisfactory technique for assuring continuous or substantially continuous operation at the optimum air/fuel ratio is through the utilization of an appropriate feedback control mechanism. In implementing suitable feedback control systems, it has been proposed to employ sensors responsive to the chemistry of the exhaust gases, that is, the heated gaseous combustion by-products, in order to control the precise air content and/or fuel content of the air/fuel mixture being provided to the engine.

One form of exhaust gas sensor which has received attention in recent years in the electrochemical form of sensor. One type of electrochemical sensor operates as an electric cell which generates a voltage potential between electroded faces or surfaces of a ceramic material when the partial pressure of oxygen of the gaseous environment to which one of the electroded surfaces is exposed is different from that to which the other surface is exposed. For example, zirconia ceramic material (zirconium dioxide having a general formula $Z_rO_2$) having an electroded surface exposed to the exhaust gas environment will generate a voltage between the electroded surfaces which is indicative of the differential partial pressure of oxygen. When the electroded surface exposed to the exhaust gases is formed of a film of catalytic material such as platinum, such sensors are known to generate a voltage which will demonstrate a virtual step function change when the exhaust gases exposed to the one electroded surface are generated by combustion of an air/fuel mixture which undergoes a rich-to-lean or lean-to-rich excursion. However such devices are known to be expensive to manufacture and to demonstrate limited life in use. In order to have a desirably rapid response time, such devices are provided with a relatively thin ceramic wall between the electroded surfaces. Such devices are thus fragile. Exposure to a substantial temperature gradient across the ceramic material renders the ceramic material prone to fracture or to formation of microcracks which can short circuit the electroded surfaces. It is also known that the exhaust gas system of an internal combustion engine is a relatively harsh environment. In order to be of practical utility over an extended period of time, any device intended to operate within the exhaust gas environment must be of rugged construction. Thus, the thinness of the ceramic material results in some loss of ruggedness.

A second type of electrochemical exhaust gas sensor employs a ceramic material which demonstrates a predictable electrical resistance change when the partial pressure of oxygen of its environment changes. An example of such a material is titania (titanium dioxide having a general formula $T_iO_2$). Such sensors can be fabricated generally in accordance with the teachings of U.S. Pat. No. 3,886,785 issued to Stadler et al., titled Gas Sensor and Method of Manufacture and assigned to the assignee hereof. Tests of such devices have shown that at elevated and substantially constant temperatures, the devices will demonstrate a virtual step change in resistance for rich-to-lean and lean-to-rich excursions of the air/fuel ratio of the combustion mixture producing the exhaust gas environment of the device.

A principal difficulty which has been encountered with such variable resistive devices resides in the fact that such devices will demonstrate a measurable resistance change which is also a function of change of the temperature of the ceramic material, for example a change of about 500° F. produces measurable resistance changes on the order of magnitude associated with a sensed rich-to-lean or lean-to-rich air/fuel mixture change have been encountered. Such a temperature variation can be encountered, depending of course to some extent on the location of placement of the sensor within an exhaust system during acceleration of the associated engine from idle speed to highway speeds. Heretofore, exhaust gas sensors which employed a variable resistance sensor ceramic have required that the temperature of the material be relatively closely controlled for reliable use in a feedback system intended to provide an internal combustion engine with very precise air/fuel ratio control.

Temperature control of the associated sensor has required the addition of expensive electronic temperature sensing and heating control systems external to the exhaust conduit and the addition of a heater element per se situated internally of, or in close proximity to, the sensor element. In order to narrow the operational range of temperature of the sensor, the sensor has been operated at the higher end of the predictable range of exhaust gas temperatures thus requiring substantially continuous application of heat energy for most of the operating cycles of the associated engine. While such devices have continued to be of rugged construction, the addition of the heater and associated electronics devoted to temperature control have increased cost and have increased statistical failure problems. An additional problem which has been encountered is a ceramic fracture problem believed to be associated with thermal shock caused by the rapid heating of the ceramic material by the heater element. For less precise operation, unheated devices have been required to be installed at a location in an exhaust gas environment where the temperature of the exhaust gases will not vary substantially for variation in the operating cycle of the associated engine.

Since variable resistance exhaust gas sensor devices are of substantially greater mechanical strength and ruggedness than are other known types of exhaust gas sensor and are not subject to the temperature gradient which is inherent in operation of a galvanic cell type of exhaust gas sensor, it is an object of the present invention to provide a variable resistance exhaust gas sensor construction which is relatively temperature insensitive. With greater particularity, it is an object of the present invention to provide a titania exhaust gas sensor construction which is capable of producing an output signal which is rendered relatively insensitive to the temperature of the surrounding environment. With greater particularity still, it is a further and particular object of the present invention to provide a variable resistance ceramic exhaust gas sensor construction which is relatively insensitive to the temperature of the surrounding medium and which need not require additional apparatus for maintenance of a substantially constant temperature. With the foregoing objective in mind, it is a further object of the present invention to provide an exhaust gas sensor which does not require the application of external heating energy. It is also a further and particular objective of the present invention to provide a means of temperature compensation for a variable resistance ceramic exhaust gas sensor whereby sensor performance over a relatively wide range of operating temperatures will be relatively temperature insensitive. In furtherance of the foregoing objectives, it is a further and particular objective of the present invention to provide a variable resistance ceramic exhaust gas sensor with temperature compensation in the form of a high temperature thermistor in a construction which is rugged in use and which does not require expensive manufacturing techniques or equipment.

As noted hereinabove, one type of electrochemical exhaust gas sensor is the electrical cell type of sensor which generates a voltage potential as a function of differential oxygen partial pressures. Such devices are commercially available, for example from Robert Bosch GmbH. Since exhaust gas sensors will find their earliest large scale commercial utility as signal generating devices for internal combustion engine feedback air/fuel ratio control circuitry, it is highly desirable to provide a variable resistance exhaust gas sensor which produces a signal which is or easily may be rendered to be compatible with the electronic circuitry designed to be used with the variable voltage generating device. It is therefore a further and particular object of the present invention to provide an exhaust gas sensor construction which principally is substantially insensitive to variation of the temperature of its environment but which additionally is, or may be rendered capable of generating a variable voltage signal compatible with the electronic control logic and the feedback control philosophy of associated electronics designed for implementation with the electric cell type exhaust gas sensors.

SUMMARY OF THE PRESENT INVENTION

The present invention provides a variable resistance exhaust gas sensor construction having a pair of electrically series connected variable resistance ceramic chip members. The chip members are supported within the hot exhaust gas environment by an elongated extending ceramic insulator member. The insulator member is sealingly received within a mounting body for threaded attachment to, and insertion of the chip members into, the exhaust system of an internal combustion engine. The insulator member includes a plurality of generally longitudinally extending bores for receipt of electrical leads to intercommunicate the chip members with electrical terminals mounted on or attached to the end of the insulator member opposite the chip members. The electrical terminal members are situated to be external to the exhaust system. The terminal members are arranged for electrical communication with utilization means, for example an electrical or electronic air/fuel ratio controller. The insulator member includes an extending annular collar surrounding the chip members and defining a well or cavity within which the chip members may be received. The collar provides for shielding of the chip members from direct impingement of exhaust gas pulsations and protects the chip members during handling prior to and during installation in an engine exhaust system.

One of the chip members comprises a porous, variably resistive, partial pressure of oxygen and temperature responsive metal oxide ceramic material which is a semiconductor at elevated temperature. The other of the chip members comprises a high temperature thermistor formed from the same or an electrically similar metal oxide ceramic material which is fabricated to be substantially nonresponsive to variations in the partial pressure of oxygen of its environment. The chip members are connected electrically in series and are arranged to define a voltage divider network. When a reference voltage is applied across the voltage divider network, the voltage appearing at the junction between the chip members may define the output voltage of the exhaust gas sensor construction. By comparing this voltage to the voltage level at either end of the voltage divider network a useful output signal may be derived. By selectively referencing to define the output signal as either the voltage drop across the sensor chip member or the voltage drop across the thermistor chip member, the resulting output signal can be rendered to be high in the region of λ values less than 1.0 or to be high in the region of λ values greater than 1.0.

BRIEF DESCRIPTION OF THE DRAWING

FIG. 6 shows a graph of the output signal voltage versus equivalence ratio, λ, for a variable resistance exhaust gas sensor according to the prior art and operated at substantially different elevated temperatures.

FIG. 7 shows a graph of the output signal voltage versus equivalence ratio, for the exhaust gas sensor according to the present invention and operated at substantially different elevated temperatures.

DETAILED DESCRIPTION OF THE PREFERRED EMBODIMENT

Figure 1:
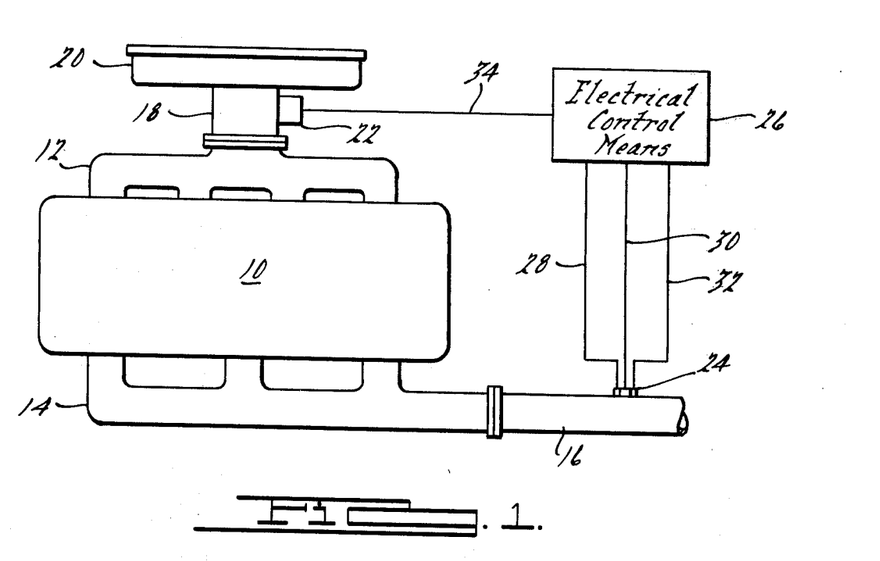
FIG. 1 is a schematic diagram illustrating an internal combustion engine having an exhaust gas responsive feedback combustion mixture control mechanism with which the exhaust gas sensor of the present invention is of utility.

Referring now to the drawing wherein like numbers designate like structure throughout the various views thereof, an internal combustion engine 10 is shown schematically in FIG. 1. Internal combustion engine 10 is provided with an intake manifold 12 and an exhaust manifold 14. Exhaust manifold 14 communicates with an exhaust gas conduit 16.

A fuel metering and delivery device 18, which may be, for example, a fuel injection system of a carburetor, is illustrated schematically as being mounted in communication with the intake end of intake manifold 12. Fuel metering and delivery device 18 is provided with an air cleaner 20 such that air ingested by engine 10 through intake manifold 12 may be drawn from the atmosphere through air cleaner 20 and through at least a portion of the fuel metering and delivery device 10. Fuel metering and delivery device 18 is further provided with an air/fuel ratio modulator means 22.

Air/fuel ratio modulator means 22 may be, for example, in the case of an electrically or electronically controlled fuel delivery system, a variable resistor arranged to control the quantity of fuel delivered to engine 10 in respect of a given quantity of air or, in the case of a mechanically or electromechanically controlled fuel delivery system such as a carburetor, a variably positionable metering orifice arranged to control the quantity of fuel delivered to engine 10 in respect of a given quantity of air. The air/fuel ratio modulator means 22 alternatively may be arranged to control a variably positionable air valve so that the quantity of air ingested by engine 10 in respect of a given quantity of fuel delivered by fuel metering and delivery device 18 may be controllably modulated.

Exhaust gas conduit 16 is provided with an exhaust gas sensor 24 according to the present invention mounted in conduit 16 so as to place the exhaust gas responsive elements of the sensor within the stream of exhaust gases flowing through conduit 16. Exhaust gas sensor 24 may be threadedly received by a suitable land or boss provided therefor on exhaust gas conduit 16. Alternatively, such a land or boss may be provided on exhaust manifold 14 whereby exhaust gas sensor 24 may be placed in closer proximity to the combustion chambers of the engine 10. In this regard, the selected location for placement of the exhaust gas sensor 24 within the exhaust system of engine 10 will be a function of the anticipated normal operating temperature of the selected location, the ease of servicing the sensor 24 in the selected location, the effects, if any, of electrical interference on or by ancillary electrical or electronic devices and general convenience. However, the selected location preferably will be upstream from the contemplated catalytic exhaust gas treatment device, not shown, and at a location exposed to the exhaust gases from all of the combustion chambers of the engine. The exhaust gas sensor 24 is arranged to communicate electrically with an electrical control means 26 over sensor electrical leads 28, 30, 32. The electrical control means 26 is arranged to communicate electrically with air/fuel ratio modulator means 22 by way of modulator means input lead 34.

Figure 2:
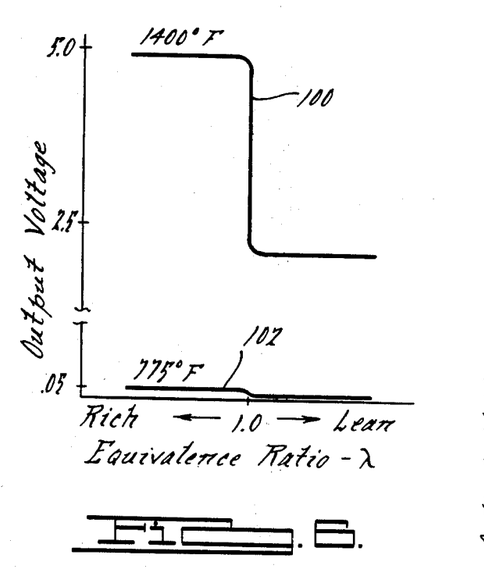
FIG. 2 illustrates, in block diagram form, an electronic combustion mixture control feedback system responsive to the exhaust gas sensor of the present invention.

Referring now to FIG. 2, a representative electrical control means 26 is illustrated in a block diagram. Reference voltage source 36 receives electrical energy, for example from the vehicle battery 38 and/or the conventional vehicle electrical charging system, now shown, via electrical bus 40. Reference voltage source 36 communicates with exhaust gas sensor 24 by way of sensor electrical leads 28, 30. Exhaust gas sensor 24 communicates via sensor electrical lead 32 with modulator control signal generator 42. Modulator control signal generator 42 also receives electrical energization from bus 40.

Modulator control signal generator 42 is adapted to generate an electrical signal on modulator means input lead 34 as a function of the voltage signal appearing on sensor electrical lead 32. Modulator control signal generator 42 is adapted to generate an output signal of a magnitude and electrical polarity which is suitably tailored to coact with air/fuel ratio modulator means 22 to increase or decrease the air/fuel ratio of the combustion mixture being provided to internal combustion engine 10 in order to provide an exhaust gas composition which will be sensed by exhaust gas sensor 24 as being the gaseous by-products of combustion of a combustible mixture having a selected, for example, stoichiometric, air/fuel ratio. Modulator control signal general 42 may operate to compare the signal received on sensor lead 32 from exhaust gas sensor signal generated by an exhaust gas composition produced by combustion of an air/fuel mixture having the desired air/fuel ratio. Deviation of the signal on lead 32 from a signal indicative of the desired value will cause a suitable signal to be generated on lead 34 to initiate correction of, for example, the fuel content of the combustible mixture. Modulator control signal generator 42 should be designed and tailored to take into account the time lag associated with the transport properties of the engine 10 and the time period required for a change in air/fuel ratio to be recognized by exhaust gas sensor 24.

Figure 3:
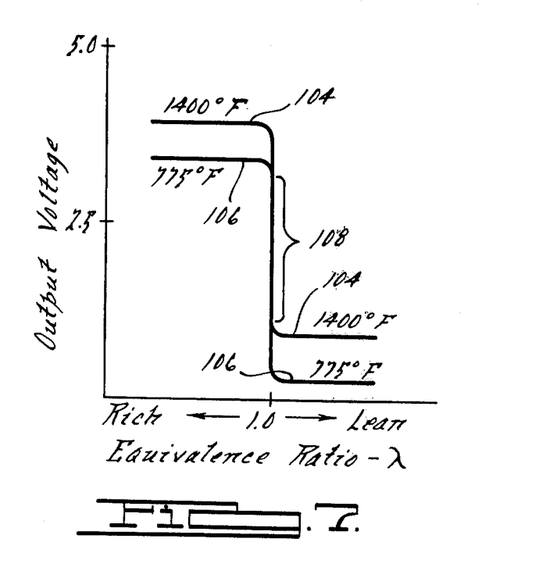
FIG. 3 illustrates the exhaust gas sensor construction of the present invention.

Referring now to FIG. 3, exhaust gas sensor 24 according to the present invention is illustrated. Exhaust gas sensor 24 is provided with a housing means 44 which is threaded as at 46 for engagement with a suitably threaded aperature provided therefor within exhaust manifold 14 or exhaust gas conduit 16. Ceramic insulator member 48 extends through housing means 44 and includes a forwardly projecting sensor support portion 50. Sensor support portion 50 includes forwardly projecting collar 52 which defines a well or cavity 54. According to the present invention, a pair of ceramic chip members 56, 58 are received within well 54. Three electrical terminal members 60, 62, 64 extend rearwardly from ceramic insulator member 48. Electrical terminal members 60, 62, 64 are adapted for receipt of suitable mating connectors, not shown, to electrically communicate exhaust gas sensor 24 with the electrical control means 26 (as shown in FIG. 1).

Figures 4, 5:
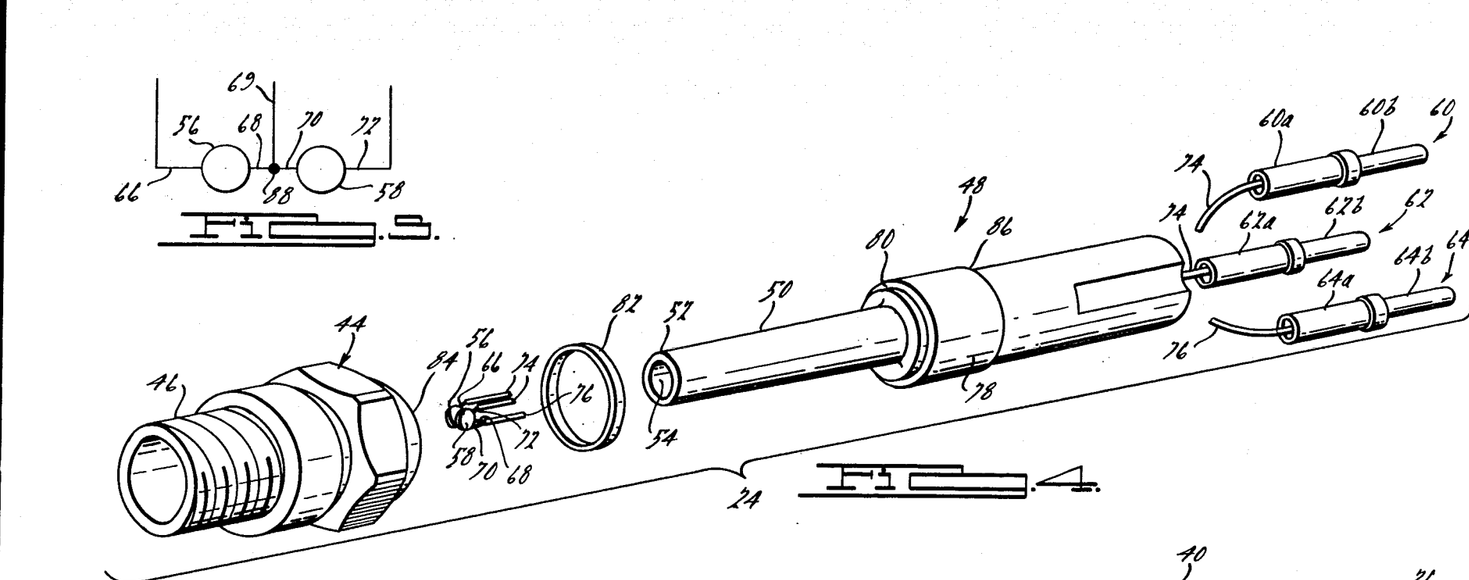
FIG. 4 illustrates the exhaust gas sensor of the present invention and according to FIG. 3 in an exploded view.
FIG. 5 illustrates the electrical series connection of the exhaust gas responsive ceramic chip members used in an exhaust gas sensor according to the present invention.

Referring now to FIGS. 3 and 4, and particularly to FIG. 4 wherein the exhaust gas sensor 24 according to the present invention is illustrated in an exploded view, the assembly of the exhaust gas sensor 24 is described. The insert portions 60a, 62a, 64a of each of the electrical terminal members 60, 62 and 64 is cemented into position within the rear portion of ceramic insulator member 48 and the terminal members 60, 62 and 64 are arranged to project a contact portion 60b, 62b, 64b of each terminal member 60, 62 and 64 rearwardly from the rear face of ceramic insulator member 48. An example of a suitable cement is Sauereisen #31. This is a catalyst activated low temperature curing cement. This cement has high acid resistance and cures to a high density. High density is of value to prevent oxygen leakage past the electrical terminals 60, 62, 64 to the sensing chip members 56, 58. Other low temperature curing, high density cements also could be used.

Each ceramic chip member 56, 58 is provided with a pair of electrical leads 66, 68, 70 and 72. Leads 66 and 72 are provided with insulating sleeve members 74. The electrical leads 68, 70 are shown being provided with a further single insulating member 76 the significance of which will be described hereinbelow with reference to FIG. 5. Insulating sleeves 74, 76 with their interiorly received electrical leads 66, 68, 70 and 72 are threaded through longitudinally extending bores or passages within, and which extend completely through, ceramic insulator member 48 from the bottom of well or cavity 54 to the rear face of ceramic insulator member 48. Electrical lead 66 and its associated insulator 74 are inserted into the insert portion 60a of electrical terminal member 60. The electrical lead 66 is electrically united with the contact portion 60b of terminal member 60. Similarly, electrical lead 72 and its associated insulator member 74 are inserted into the insert portion 62a of second electrical terminal 62. The electrical lead 72 is electrically united with the contact portion 62b of terminal member 62. The conductor formed by sensor leads 68, 70 and its associated insulator member 76 are similarly inserted into the insert portion 64a of electrical terminal 64 and the conductive portion thereof is electrically united with the contact portion 64b of terminal member 64.

The ceramic chip members 56, 58 preferably are situated completely within the well or cavity 54. Projecting collar 52 is thus operative upon insertion of the sensor assembly 24 into an exhaust system to shield the ceramic chip member 56, 58 from any solid particles which may be dislodged from the interior surface of the exhaust manifold 14 or exhaust gas conduit 16. Collar 52 also protects the electrical leads 66, 68, 70, 72 from flexure induced by pressure and exhaust gas flow fluctuations or pulsations in the exhaust gas system. Collar 52 further protects the ceramic chip member 56, 58 and their electrical leads 66, 68, 70 and 72 from possible damage during subsequent assembly and from handling damage prior to or during installation in a vehicle exhaust system.

Ceramic insulator member 48 is provided with a centrally positioned enlarged annular portion 78 which is provided with a seal receiving recess 80 at its forward shoulder. Enlarged annular central portion 78 is provided with an abutment shoulder 86 at its rear. The forwardly projecting portion 50 of ceramic insulator member 48 is inserted through seal member 82 and seal member 82 is loosely received within recess 80. The ceramic insulator member 48 is then inserted into housing means 44. The rear portion 84 of housing means 44 is then crimped or otherwise deformed into close intimate contact with rear shoulder 86 of the central portion 78 of ceramic insulator means 48 to compressively and sealingly confine seal member 82 between recess 80 and a suitably provided shoulder within the central portion of housing means 44. Seal member 82 is operative to define a fluid tight barrier to flow around insulator member 48 through housing means 44. With specific reference to FIGS. 1 and 2, seal member 82 is operative to establish a fluid tight barrier between the interior of the exhaust gas conduit 16 and the exterior of exhaust gas conduit 16.

Referring now to FIG. 5, the electrical series connection between ceramic chip members 56 and 58 and electrical leads 66, 68, 70 and 72 is illustrated. Electrical leads 68, 70 are electrically united, as by welding, brazing or soldering, at junction 88. A single electrical lead 69 extends from junction 88. With reference to FIGS. 3, 4 and 5, electrical lead 66 communicates, for example, with terminal member 60, electrical lead 72 communicates, for example, with terminal 62 and electrical lead 69 may extend through insulating member 76 to communicate sensor leads 68, 70 for example, with electrical terminal 64. With reference to FIGS. 2 and 3, electrical terminals 60 and 62 of the exhaust gas sensor 24 may be electrically communicated to reference voltage source 36 by way of conductors 28 and 30, respectively. Electrical terminal 64 may communicate the junction 88 of leads 68, 70 from ceramic chip members 56, 58 to the modulator control signal generator 42 by way of electrical conductor 32.

Reference voltage source 36 may be arranged to generate a predetermined constant voltage differential between conductors 28, 30 of, for example, five (5.0) volts. This voltage differential will be applied by sensor leads 66, 72 to the voltage divider comprised of ceramic chip members 56, 58. As will be discussed hereinbelow, the ceramic chip members 56, 58 will behave as variable resistances in the presence of the hot gases having varying oxygen partial pressure so that junction 88 will exhibit a voltage which, in the practice of our invention, will be indicative of the instantaneous oxygen partial pressure. By communicating the voltage at junction 88 to modulator control signal generator 42 a command signal may be generated for application via conductor 34 to air/fuel ratio modulator means 22 to maintain the combustible mixture provided to engine 10 at a preselected, for example stoichiometric, air/fuel ratio. By selectively determining which of leads 28, 30 is to be electrically more positive than the other of leads 28, 30 the voltage appearing at junction 88 will represent the voltage drop across either ceramic chip member 56 or ceramic chip member 58. Thus, the voltage appearing at junction 88 can be tailored to demonstrate either a low-to-high or high-to-low variation for a selected excursion through stoichiometry of the air/fuel ratio of the combustible mixture being provided the engine 10.

One of the ceramic chip members, for example, ceramic chip member 56 is a high temperature thermistor and may be fabricated according to the above noted copending, commonly assigned, patent application Ser. No. 839,700. The other of the ceramic chip members, for example ceramic chip member 58, is a partial pressure of oxygen responsive member and may be formed of titania or like material in the manner described in issued U.S. Pat. No. 3,886,785, titled Gas Sensor and Method of Manufacture, issued in the name of Henry L. Stadler et al. and assigned to the assignee of this invention. The preferred form of partial pressure of oxygen responsive ceramic chip member to be used in fabricating exhaust gas sensor 24 is the improved form described in the above-noted copending, commonly assigned, patent application Ser. No. 839,701. According to one aspect of our invention, the thermistor chip member and the partial pressure of oxygen responsive chip member are fabricated from the same metal oxide ceramic forming base material, preferably titania ($TiO_2$). The advantage of this feature is discussed hereinbelow.

According to this aspect of our invention, the thermistor ceramic chip member is formed from substantially pure titania powder. The thermistor chip member may be fabricated in much the same manner as is taught in the noted U.S. Pat. No. 3,886,785 to Stadler et al. except that the titania powder is processed to achieve a ceramic material density approaching, as closely as possible, the theoretical density of the material. Densification of the titania ceramic may be accomplished by several methods including high temperature sintering (sintering at temperatures in excess of about 2700° F.) and/or use of a titania powder having a particle size range adjusted for maximum densification during sintering. Since, according to this aspect of our invention, we desire to obtain substantially identical electrical response to temperature variation from the thermistor chip member and from the partial pressure of oxygen responsive chip member, we prefer to use identically the same titania powder material to form both ceramic chip members 56 and 58. Since uniformity of particle size consonant with obtaining a desired ceramic porosity as is necessary to produce a satisfactory partial pressure of oxygen responsive chip member and since manufacturing complexity is reduced when the same starting powders are used, we have relied upon high temperature sintering to achieve the desired densification of the thermistor chip member. While our tests have indicated that even densified titania will continue to demonstrate some resistance variation as a function of partial pressure of oxygen, we have also determined that the time rate of response of resistance changes to changes in partial pressure of oxygen increases dramatically with increasing density of the titania material. The time rate of response for densified titania increases sufficiently that, for feedback control of short duration air/fuel ratio deviations in an internal combustion engine, the dependency of the thermistor resistance on partial pressure of oxygen and particularly changes in resistance induced by changes of partial pressure of oxygen in the exhaust gas environment can be ignored.

The preferred method of fabricating the partial pressure of oxygen responsive ceramic chip member involves the preparation of a substantially pure titania powder. As titania has two phases, the anatase phase and the rutile phase, and the rutile phase is the high temperature stable phase, the titania powder should be comprised of a substantial majority of rutile phase material. In order to convert anatase phase material to rutile phase material, the material may be calcined, for example for two (2) hours at 2100° F., and then ball milled to produce powder having the desired small particle sizes with the majority of the powder being rutile phase material. Calcining also improves the purity of the powder by volatilizing any volatilizable impurities. The powder should have 100% of the particles smaller in size than 20 microns and should have a substantial majority of the powder with a particle size smaller than about 10 microns. The processed powders may then be ball milled with an organic binder solution to form a slurry. The slurry may thereafter be cast, formed onto a tape or sheet of material after which the slurry may be air dried, to form a sheet or tape of material. Suitable sized and shaped wafers of the material may then be cut from the tape for further processing. A pair of lead wires may be inserted into the chip elements and the chip elements may thereafter be sintered to a pyrometric cone equivalent number 9. This sintering will cause individual grains of the ceramic material to become united with neighboring grains along contacting surfaces while preserving the intergranular porosity desired for rapid response of the sensor to changes in oxygen partial pressure. After the partial pressure of oxygen responsive chip elements have been matured, the matured ceramic elements may be impregnated with a 1:1 solution of 2% chloroplatinic acid and formaldehyde.

Impregnation may be accomplished by immersing the sensor chip elements in the 1:1 solution and evacuating the container to remove entrapped air. The solution is allowed and urged to flow through the porous sensor element so that substantially all interior sensor granular surfaces are exposed to the solution. The impregnated elements are then air dried and heated in air to a temperature of approximately 1300° F. for a period of approximately four (4) hours to cause reduction of deposited chloroplatinate salts to finely divided particles of metallic platinum and to sinter the platinum particles to the associated ceramic grains within the sensor ceramic.

In a second and presently preferred impregnation process, a 1:1 solution of 5% chloroplatinic acid and formaldehyde is used. In the second process, the liquid immersed sensor elements are heated in air at a temperature of approximately 1650° F. for a period of approximately six (6) hours. It will be appreciated that various strength solutions of catalytic agent forming material may be used and that these different solutions may require slightly different processing times and temperatures to accomplish deposition of the catalytic agent on the grains and particularly the interior grains of the ceramic material comprising the porous sensor body and subsequent sintering of the catalytic material to the ceramic.

Referring now to FIG. 6, response curves are graphed illustrating the performance of a titania exhaust gas sensor fabricated according to the prior art and operated over a range of temperatures comparable to that encountered in an automotive internal combustion engine exhaust system. FIG. 6 illustrates output voltage plotted along the ordinate and an air/fuel equivalence ratio $\lambda$ plotted along the abscissa. The data for preparing the FIG. 6 graph was obtained by connecting a 100 K ohm fixed resistor electrically in series with and remote from a titania partial pressure of oxygen responsive ceramic chip, by applying a fixed voltage of five (5.0) volts across the series connection, and by measuring the voltage drop across the fixed resistor. It should be noted here that the generation of an output voltage signal based on a fixed applied voltage is intended to produce an output voltage characteristic comparable to that produced by the galvanic cell or zirconia type of electrochemical exhaust gas sensor. By measuring the voltage drop across the fixed resistor, the resulting voltage signal is higher for equivalence ratios less than one. If voltage signal reversal is desired (i.e., a voltage signal higher for equivalence ratios greater than one), the voltage drop across the sensor chip per se would be measured.

The sensor was then exposed to hot gaseous mixtures identical with the exhaust gases produced by combustion of combustible air/fuel mixtures having lambda ($\lambda$) values ranging from less than 1 to lambda ($\lambda$) values greater than 1. In gaseous environments maintained at a temperature of about 1400° F., the voltage appearing at the junction of the sensor chip member and the fixed resistor demonstrated the voltage variation identified by curve 100. It will be noted that at an equivalence ratio of lambda ($\lambda$) substantially equal to 1, curve 100 undergoes a dramatic voltage change, a virtual step function change, with the output voltage going from a value slightly less than the applied voltage value to a voltage value substantially less than half of the applied voltage value.

The curve identified as 102 is based on data similarly derived for tests conducted with the gaseous mixture maintained at a temperature of about 775° F. It will be noted that curve 102, while it may demonstrate a voltage change comparable to a step function change at lambda ($\lambda$) values equal to 1, demonstrates only a small voltage change when compared to the change demonstrated by curve 100. Furthermore, it will be noted that curve 102 does not coincide at any point with the curve 100. Intermediate levels of gaseous temperature would produce response curves lying intermediate to the two curves 100 and 102. It will be appreciated, therefore, that in the application of a prior art sensor to a feedback fuel control system as generally set forth in FIG. 2, the system would of necessity have to be able to identify the specific temperature of the exhaust gas environment in order to determine the equivalence ratio associated with a particular measured output voltage value. Alternatively, maintenance of the sensor at the elevated temperature would allow actual exhaust gas temperature to be ignored. It will be appreciated, therefore, that very sophisticated electronics would be required in order to interface an exhaust gas sensor according to the prior art which was intended to operate over a range of temperatures as a sensor for a feedback fuel control system.

Referring now to FIG. 7, a graph illustrating the output voltage characteristic for an exhaust gas sensor construction according to the present invention is illustrated. The data represented on the graph of FIG. 7 was derived from an exhaust gas sensor circuitry as illustrated in FIG. 5 wherein a fixed reference voltage of five (5.0) volts was applied across sensor leads 66, 72 and an output voltage was measured on sensor lead 69 as the voltage drop across the thermistor chip member. Voltage graph 104 illustrates the output voltage appearing on sensor lead 71 when the sensor according to the present invention was exposed to a hot gaseous environment with the temperature thereof maintained at about 1400° F., and the partial pressure of oxygen was varied from values representing lambda ($\lambda$) values less than 1 to lambda ($\lambda$) values greater than 1.

When the same sensor was exposed to a hot gaseous environment maintained at a temperature of approximately 775° F. and the partial pressure of oxygen of the gaseous environment was varied from lambda ($\lambda$) values less than 1 to lambda ($\lambda$) values greater than 1, the output voltage signal appearing on sensor lead 69 demonstrated an output voltage signal variation as represented by curve 106. It will be appreciated that intermediate temperature values would produce curves lying intermediate to curves 104 and 106. It will be specifically noted that curves 104 and 106 demonstrate a substantial region of signal voltage overlap identified by reference numeral 108. This region of overlap also coincides with the region of large scale output voltage signal variation for slight changes in lambda value.

In the application of an exhaust gas sensor 24 according to the present invention to a feedback system for maintaining the air/fuel ratio of the combustible mixture provided to the engine 10 at stoichiometry, a designer may conveniently select an output voltage level corresponding to a voltage within overlap portion 108 and may thereafter reliably regard sensed voltage values greater than the selected reference as indicating an equivalence ratio or lambda value less than 1, i.e., a value indicative of rich engine operation. Similarly, sensed voltage values less than the selected reference would identify engine operation with lambda values greater than 1, i.e., values indicating lean engine operation.

By fabricating the thermistor chip member from the same ceramic material as the partial pressure of oxygen responsive chip member, both chip members 56, 58 will demonstrate comparable resistance responses to the temperature of their environment. The effect of temperature change on the output signal may thus be readily compensated for as will be evident from the discussion of FIGS. 8, 9, 10 and 11 which follows. While use of a high temperature thermistor per se would generally achieve this result, it will be appreciated that the electrical behavior of the thermistor chip member may be more closely matched to the electrical behavior of the sensor chip member initially and throughout the operating life of the exhaust gas sensor 24 since aging effects and performance changes responsive to the environment will be comparable.

Figure 8:
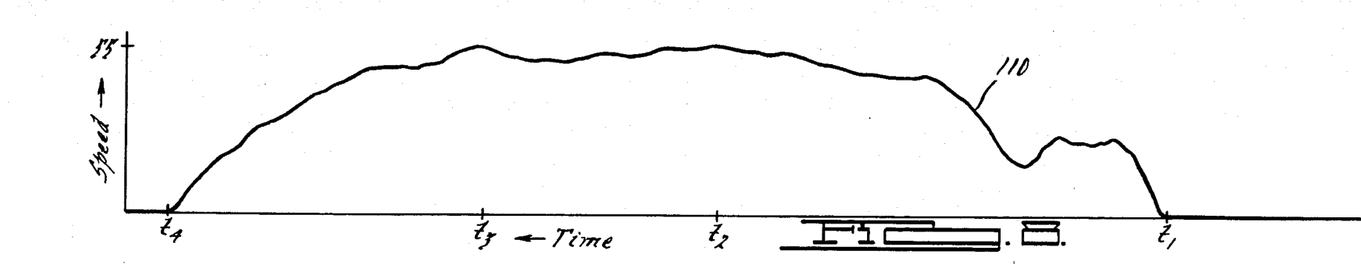
FIG. 8 is a graph illustrating engine speed graphed as a function of time.

Referring now to FIG. 8, a graph 110 illustrating vehicle speed as a function of time is shown for a vehicle having an internal combustion engine 10 equipped with a feedback fuel control system responsive to an exhaust gas sensor 24 according to the present invention. Vehicle speed varies from zero miles per hour, in the interval from time $t_0$ $t_1$, corresponding to an engine start-up and idle with vehicle accelerations up to speeds of approximately 55 miles per hour for example as, indicated by the speed peaks associated with time $t_2$ and $t_3$ and return to zero speed at time $t_4$. In FIG. 8, vehicle speed is graphed as a function of time with time $t_0$ occurring at the right hand edge of the graph and increasing time extending leftward. For zero vehicle speed, the associated internal combustion engine 10 will be operating at idle and successive engine firing events will occur with a relatively large time interval therebetween. As engine speed increases, the firing events will occur closer together in time. At increased engine speeds, with the firing events occurring more closely spaced in time, it will be appreciated that the temperature of the exhaust gases and the associated engine parts will be elevated. Thus higher exhaust gas temperatures are associated with higher vehicle and engine speeds.

Figure 9:
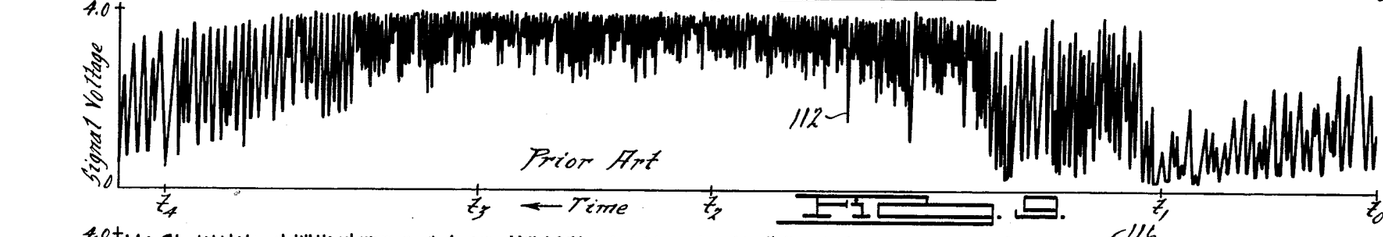
FIG. 9 is a time based graph, corresponding to the FIG. 8 graph, of the signal generated by the prior art variable resistance exhaust gas sensor operating in the exhaust system of the engine whose speed is graphed as a function of time in FIG. 8.

Referring now to FIG. 9, a graph 112 of the output voltage generated by an exhaust gas sensor according to the prior art operated as described with reference to FIG. 6 in the variable temperature exhaust gas environment generated by the engine operated according to the speed graph 110 of FIG. 8 is shown. As shown in this Figure, the sensor output signal voltage fluctuates over a portion of the lower voltage region in that portion of graph 112 corresponding to the low engine speed mode operation of the engine which produced the FIG. 8 graph, from time $t_0$ to $t_1$. As the engine accelerates, the voltage fluctuation shifts from lower values to higher values in the portion from time $t_1$ to $t_4$. It will be noted that in the time domain from time $t_2$ to $t_3$ there is virtually no voltage output signal overlap with the signal generated during the time interval from $t_0$ to $t_1$. It follows therefore that selection of a signal voltage level for comparison to define lambda values greater than 1 or less than 1 for the associated engine would not be practicable. Thus, the prior art sensor, when operated at the varying temperatures which normally occur in an internal combustion engine exhaust produces an output signal which requires further information for processing to result in a signal usable as a feedback fuel control input signal. It should be noted here that the data used to generate graph 112 was derived from an exhaust gas sensor according to the prior art in an exhaust gas sensor conduit for an engine which did not include exhaust gas sensor response feedback fuel control. Thus, the rapid fluctuations of the output voltage indicate normally occurring rich-to-lean and lean-to-rich excursions in the combustible mixture.

Figure 10:
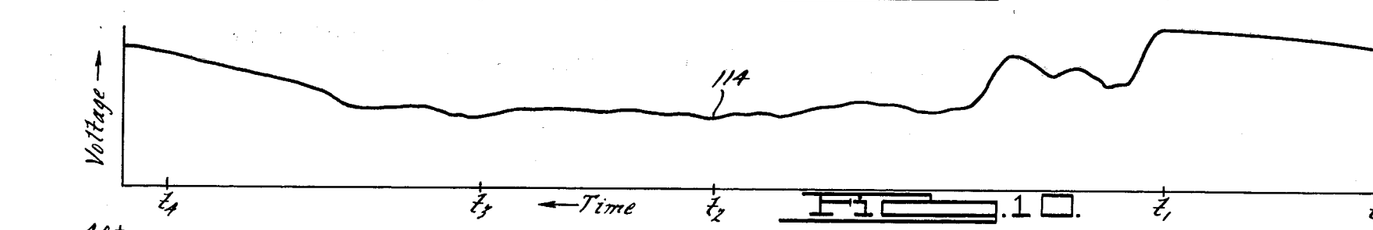
FIG. 10 is a time based graph, corresponding to the FIG. 8 graph, of the voltage drop across the thermistor chip of an exhaust gas sensor fabricated according to the present invention and operating in the exhaust system of the engine whose speed is graphed as a function of time in FIG. 8.

Referring now to FIG. 10, voltage graph 114 illustrates the voltage drop across the thermistor member, for example ceramic chip member 56, in an exhaust gas sensor according to the present invention and operated, as described with reference to FIG. 7, in the variable temperature exhaust gas environment generated by the engine operated according to the speed graph 110 of FIG. 8. During the time interval from time $t_0$ to $t_1$, the voltage drop measured across thermistor member 56 is relatively high. During the time interval from time $t_2$ to $t_3$, however, the voltage drop appearing across thermistor element 56 is relatively low. Thus, for low temperature environments, a larger voltage drop will be recorded across thermistor member 56 than is recorded across thermistor member 56 under comparatively higher temperature conditions.

Figure 11:
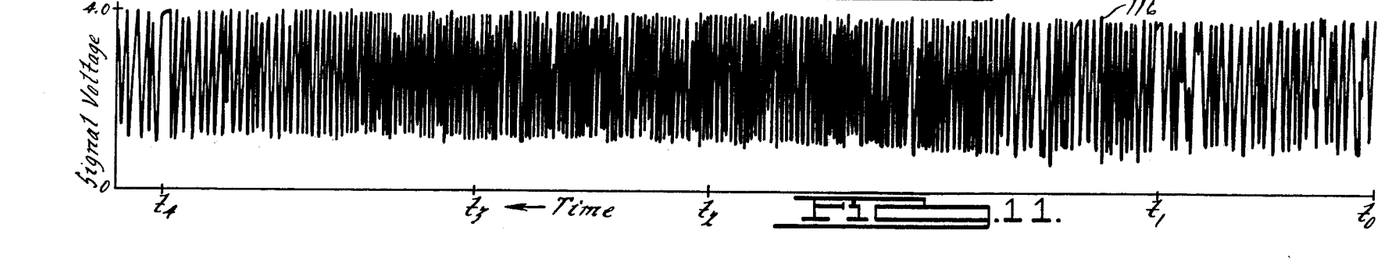
FIG. 11 is a time based graph, corresponding to the FIG. 8 graph, of the voltage signal derived from the junction of the network illustrated in FIG. 5 and illustrating the electrical performance of the exhaust gas sensor according to the present invention.

Referring now to FIG. 11, the voltage signal generated across the partial pressure of oxygen responsive member, for example ceramic chip member 58, is illustrated as voltage graph 116. During the time interval from time $t_0$ to $t_1$, the voltage graph 116 demonstrates peak-to-peak voltage excursions which are greater in magnitude than are demonstrated during the comparable time period by the prior art sensor as illustrated by graph 112. Furthermore, while the minimum voltage values are comparable, the maximum voltage values are substantially greater. During the time interval from time $t_2$ to $t_3$, the voltage graph 116 demonstrates substantially greater voltage magnitude excursions than are demonstrated during the comparable time period by the prior art sensor as illustrated by graph 112. Furthermore, while the maximum voltages are comparable in magnitude, the minimum voltages recorded during the time interval time $t_2$ to $t_3$ are substantially lower. It will be observed that there is substantially no significant difference between the minimum voltages recorded during the time interval time $t_0$ to $t_1$ and during the time interval time $t_2$ to $t_3$ and that conversely there is substantially no significant difference between the maximum voltages demonstrated during the time interval time $t_0$ to $t_1$ when compared with those measured during the time interval time $t_2$ to $t_3$.

It will thus be apparent that the signal voltage measured and recorded on graph 116 may be readily used to derive useful lambda value information for the associated engine. The temperature fluctuation which occurs normally as a result of variation in the speed of the associated engine and which prevented the prior art sensor from being directly usable to indicate lambda values for the associated engine has been eliminated by the inclusion of the series connected thermistor. The electrical response of the thermistor has been adequate to eliminate temperature fluctuation as an adverse influence on the voltage signal of the sensor.

It will be appreciated that the instant invention readily accomplishes its stated objective. An exhaust gas sensor construction is provided which permits substantially direct readings to indicate lambda values for the associated engine. The sensor construction places the partial pressure of oxygen responsive ceramic element and the temperature compensating thermistor element in close physical proximity to each oth other in the exhaust gas stream. By providing an exhaust gas sensor with a partial pressure of oxygen responsive member and a thermistor member which are fabricated from essentially the same ceramic material, long term aging effects, electrical response and change in electrical response to conditions within the exhaust gas system other than oxygen and temperature will be substantially identical during the useful life of the exhaust gas sensor. The construction provided by the instant invention is relatively rugged in use and provides substantial protection for the ceramic members and their electrical leads during assembly and fabrication of the sensor itself and during installation of the sensor within an exhaust gas system of an internal combustion engine.

We claim:

1. An improved sensor of the type adapted for installation in an exhaust manifold or exhaust conduit for conveying exhaust gases from an internal combustion engine, the improved sensor being responsive to the partial pressure of oxygen in the exhaust gases to which the sensor is exposed and having an electrical characteristic which varies, when the sensor is at operating temperatures in the range from about 700° F. to about 1500° F., with the partial pressure of oxygen in the exhaust gases, the sensor comprising:

a housing adapted for connection to the exhaust manifold or exhaust conduit of an internal combustion engine;

a ceramic insulator having a forwardly projecting sensor element support portion and a rearwardly extending terminal portion received within the housing and positioned such that the forwardly projecting sensor element support structure is adapted to project into the exhaust manifold or exhaust conduit when the housing is connected thereto as adapted therefor, the forwardly projecting portion of said insulator including a thin-walled cavity and at least first, second and third passages extending from the bottom of the cavity to the rearward portion of the insulator;

at least three electrical terminals each positioned within one of the three passages at the rearwardly extending terminal portion of the insulator;

a pair of series-connected metal-oxide ceramic sensing elements supported within the cavity of the insulator, each of the sensing elements having at least two lead wires embedded therein, a lead wire from one of said pair of sensing elements being electrically connected to a lead wire of the other of the sensing elements, a second lead wire from said one of said pair of sensing elements passing through a first passage in the insulator, a second lead wire from the other of said pair of sensing elements passing through a second passage in the insulator, and a third lead wire passing through a third passage in the insulator, the third lead wire being electrically connected to the electrically connected lead wires of said one and the other of said pair of sensing elements, the lead wires in the first, second and third passages of said insulator being connected, respectively, to the three electrical terminal members received within the passages, the lead wires from the sensing elements being operative to support the sensing elements in the cavity of the insulator, the cavity having a depth sufficient to shield the sensing elements from the direct flow of gaseous products of combustion in the exhaust manifold or exhaust conduit; and said pair of sensing elements being exposed on all sides thereof to exhaust gases within the exhaust manifold or exhaust conduit, said one of said sensing elements having an electrical resistance which varies as a function of the temperature to which it is exposed and not substantially as a function of the partial pressure of oxygen to which it is exposed and the other of said sensing elements having an electrical characteristic responsive to both the temperature to which it is exposed and the partial pressure of the oxygen in the exhaust gases to which it is exposed when at a temperature within the range from about 700° F. to about 1500° F.

2. The sensor according to claim 1, wherein said one of said pair of sensing elements is a thermistor.

3. The sensor according to claim 2 wherein said thermistor is comprised of titania ceramic material.

4. The sensor according to claim 2 wherein the other of said sensing elements is a partial pressure of oxygen responsive ceramic which demonstrates a variable resistance in the pressure of variation in oxygen partial pressure.

5. The sensor according to claim 4 wherein the partial pressure of oxygen responsive ceramic sensing element is comprised of titania.

6. The sensor according to claim 1 including gas tight seal means compressively confined between said housing and said insulator means.

7. The sensor according to claim 5, wherein the thermistor is comprised of titania ceramic material substantially denser than the titania partial pressure of oxygen responsive sensing element whereby oxygen responsive sensitivity is greatly reduced.

8. An improved gas sensor of the type which employs a first variably resistive element to produce an electrical resistance change, as a function of the composition of a gas to be sensed, in a circuit including a second variable resistive element that is connected in series with said first variable resistive element and that is employed to compensate for temperature variations of said sensor when exposed to such gas, said improved sensor comprising:

said first element being formed from a porous metal oxide ceramic material having first and second electrical leads therein, said metal oxide having an electrical resistance which varies both as a function of its temperature and as a function of the partial pressure of oxygen in the gas to be sensed;

said second element being formed from a metal oxide ceramic material similar to said metal oxide ceramic material of said first element but having a ceramic material density greater than that of said first element, thereby to reduce, as compared to the ceramic of said first element, the time rate of response of the ceramic of said second element to the partial pressure of oxygen, said ceramic of said second element having an electrical resistance which varies as a function of its temperature substantially in the same manner as the temperature variation of said ceramic of said first element, and said ceramic material of said second element having first and second electrical leads therein, said second electrical lead of said first element having a junction formed with said first electrical lead of said second element, the electrical impedence between said junction and said second lead of said second element being the impedence of said ceramic material of said second element between first and second leads therein;

whereby, upon application of a reference voltage across said first lead of said first element and said second lead of said second element, a variation in voltage across said first and second leads of said first element occurs as a function of the partial pressure of oxygen of the gas to which said elements are then exposed, said variation being substantially independent of the temperature of said elements over a temperature range.

9. An improved gas sensor as in claim 8, wherein said first and second metal oxide ceramic elements are made from titania powder, the titania powder of said first element being processed differently than that of said second element, thereby to permit said second element to acquire said density greater than that of said first element.